United States Patent [19]

Hufford

[11] 4,188,392
[45] * Feb. 12, 1980

[54] ANTIMICROBIAL COMPOSITIONS

[75] Inventor: Charles D. Hufford, Oxford, Miss.

[73] Assignee: The University of Mississippi, University, Miss.

[*] Notice: The portion of the term of this patent subsequent to Jun. 6, 1995, has been disclaimed.

[21] Appl. No.: 887,932

[22] Filed: Mar. 17, 1978

Related U.S. Application Data

[63] Continuation-in-part of Ser. No. 596,282, Jul. 16, 1975, Pat. No. 4,093,717.

[51] Int. Cl.$^2$ ............................................. A61K 31/47
[52] U.S. Cl. .................................................... 424/258
[58] Field of Search ........................................ 424/258

[56] References Cited

U.S. PATENT DOCUMENTS 4,093,717   6/1978   Hufford ................................. 424/258

OTHER PUBLICATIONS

Journal Organic Chemistry, vol. 25: pp. 1389–1390, (Aug. 1960), and vol. 26: pp. 4143–4144, (Oct. 1961).
J. Pharm. Soc. Japan, vol. 82: pp. 616–618 & pp. 1199–1202 (1962).
J. Pharm. Soc. Japan, vol. 86: pp. 124–128 (1966).

Primary Examiner—Donald B. Moyer
Attorney, Agent, or Firm—William D. Stokes

[57] ABSTRACT

Antimicrobial compositions useful in mammal and plants comprising liriodenine, dehydroglaucine, liriodenine methiodide and oxoglaucine methiodide compounds and mixtures thereof. The antimicrobial compositions are particularly useful against Gram positive bacteria, acid fast bacteria and fungi and yeast.

10 Claims, No Drawings

ANTIMICROBIAL COMPOSITIONS

This application is a continuation-in-part of application Ser. No. 596,282 filed July 16, 1975 now U.S. Pat. No. 4,093,717 issued June 6, 1978.

FIELD OF INVENTION

The present invention is related to antimicrobial agents and more specifically to antimicrobial activity, particularly antibacterial and antifungal, of certain alkaloid compounds and derivatives of specific alkaloid compounds which may be extracted from the heartwood of the tulip poplar tree, *Liriodendron tulipifera* L. Specifically, the invention relates to antimicrobial compositions comprising liriodenine, liriodenine methiodide and dehydroglaucine, and oxoglaucine methiodide and mixtures thereof.

BACKGROUND OF THE INVENTION

During the last few decades an intensive effort has been made to discover new, clinically useful antimicrobial compositions. Although more than a thousand antibiotics have been discovered, few are found to be of significant antimicrobial use. To be useful an an antimicrobial agent, a substance must have a low toxicity for host cells and a high toxicity for the disease causing microorganism. In other words, the antimicrobial agent must posion the parasite and cause little or no damage to the cells of the host. It is for this reason that a substantial number of the known antimicrobials are unsatifactory. In other words, they are not selective in their action on cells and thus interfere with natural mammaliam or plant defense mechanisms. Certain disease causing microorganisms remain serious problems and some of the major antimicrobials have considerable drawbacks in terms of limited antimicrobial spectrum or serious side effects. These factors necessitate a continuing search for new antimicrobial agents.

SUMMARY OF THE INVENTION

The present invention provides relatively non-toxic and non-phytotoxic antimicrobial compositions which may be synthetically prepared or obtained from an extract of the heart-wood of *Liriodendron tulipifera* L. The compounds of the invention successfully overcome the disadvantages of the vast majority of the known antimicrobial compositions. The antimicrobial composition of the invention comprises a compound selected from the group consisting of dehydroglaucine, liriodenine, liriodenine methiodide, or oxoglaucine methiodide or mixtures thereof. The inventive compositions when prepared for use in mammal are admixed with a non-toxic pharmaceutically diluent carrier and may be effectively administered systematically or topically. For plant use a foliar spray is preferred. Among the pharmaceutically acceptable carriers for oral administration in mammals are starch, dextrose, sucrose, lactose, gelatin, agar stearic and acacia, aqueous hydrochloride salt solutions or edible oils e.g., corn or peanut oil. For mammalian topical administration, any inert ointment base or cream is satisfactory such as petroleum, water soluble ointment base, hydrophilic ointment and the like. For mammalian use, it may be appreciated that the compounds of the invention may be administered intraperitoneally, intravenously and intramuscularly in suitable pharmaceutical carriers. For treatment of plant diseases, the compounds of the invention are administered to the plant foliage by suitable agriculturally inert spray carriers, for example, water. For purposes of this application the phrases "pharmaceutically acceptable carrier" and "agriculturally inert carrier" include non-toxic and non-phytotoxic carriers for the compounds when treating plants or mammal.

DETAILED DESCRIPTION OF THE INVENTION

It was discovered that an alcoholic extract of the heartwood of L. tuliperifera exhibited an extraordinary inhibitory activity against several disease causing microorganisms such as *Staphylococcus aureus, Mycobacterium smegmatis, Candida albicans, Aspergillus niger, Bacillus subtilis, Saccharomyces cerevisiae, Puccinia graminis, Plasmopora viticola, Erysiphe polygoni, Phytophthora infestans, Botrytis fabae, Piricularia oryzae,* and *Helminthosporium teres.* It was also discovered that the substituents of the alcoholic extract of the inventive composition could be divided into alkaloid and non-alkaloid fractions. It was unexpectedly discovered that the antimicrobial activity is exhibited primarily by the alkaloid fractions.

Chromatographic separation of the extracted constituents yielded four alkaloid fractions, namely glaucine, dehydroglaucine, liriodenine and michelalbine. Although it has been previously reported that oxoglaucine is a naturally occuring alkaloid of the heartwood of L. tulipifera, none of this compound, beyond trace amounts, was found in the extract. Oxoglaucine was, however, prepared by oxidation of the glaucine found.

The antimicrobial activity of the extract of the heartwood of *Liriodendron tulipifera* L., the four alkaloid fractions of the extract, and compounds selected from the group consisting of liriodenine, liriodenine methiodide, dehydroglaucine, oxoglaucine methiodide and mixtures thereof were treated with the following organisms.

*Staphylococcus aureus* ATCC 6538
*Escherichia coli* ATCC 10536
*Mycobacterium smegmatis* ATCC 607
*Pseudomonas aeruginosa* ATCC 15442
*Candida albicans* ATCC 10231
Saccharomyces cerevisiae ATCC 9763
*Aspergillus niger* ATCC 16888
*Bacillus subtilis* ATCC 6633
*Puccinia graminis* f. sp. tritici race 15B-2
*Plasmoporo viticola*
*Erysiphe polygoni*
*Phytophthora infestous*
*Botrytis fabae*
*Piricularia oryzae*
*Helminthosporium teres*

Bacterial test organisms were cultured in Eugonagar and Eugonbroth (BBL), and some fungi and yeasts causing diseases in humans were cultured in Mycophil (BBL) agar and broth. Antimicrobial activity of the foregoing microorganisms were recorded as the width (in millimeters) of the clear zone of inhibition surrounding the agar well. The pathogenic microorganisms causing diseases in plants are host specific and are cultured in various mediums, for example, wheat dextrose agar (*Piricularia oryzae*), bean leaves (*Erysiphe polygoni*), oatmeal agar (*Botyris fabae*), grape leaves (*Plasmopora viticola*), wheat seedlings (*Puccina graminis*), lima bean agar (*Phytophtora infestans*), potato-dextrose agar (*Helminthosporium teres*).

Of the six aforementioned compositions tested, only liriodenine and deydroglaucine exhibited antimicrobial activity. Methiodide derivatives of liriodenine and oxoglaucine were prepared which exhibited an enhanced antmicrobial activity. Liriodenine, liriodenine methiodide and oxoglaucine methiodide also exhibited antimicrobial activity against plant pathogens. The antimicrobial activity of the inventive compounds is set out in Table 2 and 3 described in detail hereinafter.

EXAMPLE I 2.2 kg of air-dried, ground heartwood of L. tulipifera was extracted with ethanol USP by percolation at room temperature until a negative alkaloid test of the percolate was observed. The solvent was removed at 40° C. under reduced pressure leaving 71 g. of residue. The residue exhibited antimicrobial activity.

35 g. of the residue was partitioned between 125 ml. each of ether and 2% citric acid. The ether layer was extracted twice more with 125 ml. of 2% citric acid, filtered to remove some interfacial solids, dried with $Na_2SO_4$, and evaporated to dryness to yield 8.6 g. of residue which exhibited no antimicrobial activity. The interfacial solids weighing 5.8 g. were alkaloid negative and exhibited no antimicrobial activity.

The aqueous citric acid layers were combined, adjusted to pH 9-10 with ammonia, and extracted three times, each with 1 liter of chloroform. The aqueous layer was neutralized; a portion was evaporated to dryness and found to exhibit no antimicrobial activity. The combined chloroform layers were dried ($Na_2SO_4$) and evaporated to yield 6.2 g. of residue which exhibited antimicrobial activity.

The 6.2 g. of chloroform soluble residue was separated into tertiary phenolic and nonphenolic fractions by dissolving it in 250 ml of chloroform and extracting three times, each with 250 ml. of 5% sodium hydroxide solution. After drying, the chloroform solution was evaporated leaving 4.7 g. of tertiary nonphenolic alkaloids which possessed all of the antimicrobial activity.

A 2 g. portion of the crude nonphenolic fraction was dissolved in chloroform and chromatographed over 200 g. of aluminum oxide (Woelm, neutral, grade III). The solvents used were: 300 ml. chloroform; 500 ml. 1% of methanol in chloroform; 300 ml. of 2% methanol in chloroform; 400 ml. of 16% methanol in chloroform; and finally the column was washed with 50% methanol in chloroform. The fractions (20 ml. each) were evaporated in tared flasks, combined according to their weights and to their similarity on TLC, and then assayed for antimicrobial activity as described in Example V below. Thin layer chromatographic analyses were carried out on Aluminum Oxide G coated plates using 4% methanol in chloroform as solvent and Dragendorff's reagent. The assay results are tabulated in Table 1:

Table 1

| Chromatographic Separation of Tertiary Nonphenolic Fraction | | | |
|---|---|---|---|
| Fraction Number | Fluent | Wt. of Residue in mg | Remarks |
| 1-11 | $CHCl_3$ | 65 | nonalkaloidal, inactive* |
| 12-19 | $CHCl_3$; | | crystaline residue, glaucine, dehydro- |
| | 1% $CH_3OH$—$CHCl_3$ | 400 | glaucine, active |
| 20-32 | 1% $CH_3OH$—$CHCl_3$ | 728 | amphorphus residue, inactive* |

Table 1-continued

| Chromatographic Separation of Tertiary Nonphenolic Fraction | | | |
|---|---|---|---|
| Fraction Number | Fluent | Wt. of Residue in mg | Remarks |
| 33-40 | 1% $CH_3OH$—$CHCl_3$ | 118 | yellow solid, liriodenine, active |
| 41-51 | 2% $CH_3OH$—$CHCl_3$ | 206 | crystaline residue, michelalbine, inactive* |
| 52-65 | 2% $CH_3OH$—$CHCl_3$ | 84 | amphorphus residue, inactive* |
| 66-90 | 16% $CH_3OH$—$CHCl_3$ | 30 | amphorphus residue, inactive* |
| wash | 50% $CH_3OH$—$CHCl_3$ | 300 | amphorphus residue, inactive* |

*No activity was observed against any of the test organisms.

EXAMPLE II

Dehydroglaucine was isolated from the Fraction 12-19 of Example I and found to exhibit all of the antimicrobial activity in that Fraction.

2.4 g. of Fraction 12-19, compelled from several columns as described in Example I, were chromatographed over 200 g. of Silica Gel G using ether as the eluent. The Silica Gel G was slurried with water first, dried at 110° C. for 12 hours, and sieved through an 80 mesh sieve before use.

The first 125 ml. of eluent contained no alkaloids, but the next 150 ml. yielded a crude alkaloid (115 mg.) which was crystallized from alcohol to yield 59 mg. of slightly colored plates (mp 113°-115° C.). Subsequent recrystallizations raised the melting point of the pale yellow plates to 121°-122° C. The mass spectrum exhibited a parent ion at m/e 353. The UV spectrum showed maxima at 260 and 332 nm while the NMR indicated at 1H singlet at δ 9.60 (Ar-H) and a 3H singlet at δ 3.01 (N—$CH_3$). This data is characteristic of dehydroaporphine alkaloids. Direct comparison of mp, TLC, UV and IR of this sample with a known sample of dehydroglaucine prepared by oxidizing glaucine with potassium permanganate confirmed the identity.

Melting points were determined on a Thomas-Hoover Unimelt melting point apparatus and are uncorrected. IR spectra were run in potassium bromide or chloroform using a Perkin-Elmer 257 or Beckman IR-33 infrared spectrometer. NMR spectra were recorded on a JEOL C-60 HL spectrometer using deuterated chloroform as solvent and tetramethylsilane as the internal standard; chemical shifts are reported in δ (ppm) units. UV spectra were obtained in methanol on a Beckman ACTA III spectrophotometer. Mass spectral data were obtained on a DuPont-CDC 492 spectrometer.

EXAMPLE III

Liriodenine was isolated from Fraction 33-40 of Example I and contained all of the antimicrobial activity in this fraction.

Crystallization of the residue of Fraction 33-40 of Example I (118 mg.) from chloroform yield 85 mg. of yellow needles having a mp of 280°-281° C. The mp, IR, and UV, determined in the same manner as described in Example II, were consistent with data reported for the yellow alkaloid, liriodenine, as reported by M. A. Buchanan and E. E. Dickey in *J. Oreg. Chem.* Vol. 25, p. 1389 (1960). Direct comparison of mp, mmp, IR and UV with a known sample of liriodenine confirmed the identity.

EXAMPLE IV

Liriodenine was also prepared by synthesis from nitrotoluene as structurally shown in the reaction chart set out below. A detailed description of the synthesis is as follows: (the numerials refer to the structural compounds in the reaction chart).

A mixture of nitrotoluene (1) (6.85 g., 0.05 mole), sodium ethoxide (1.25 g. powdered sodium, 5 g. absolute ethanol), and 7.8 g. (0.05 mole) of ethyloxalate in 50 ml. of absolute ether was refluxed for eighteen hours. The reaction mixture, after cooling, was extracted with 20 ml. of 2 N sodium hydroxide solution. The aqueous layer was acidified with 2 N hydrochloric acid and extracted with 3×20 ml. chloroform. The chloroform layer was evaporated and the residue (7.3 g.) was dissolved in 40 ml of 2 N sodium hydroxide and oxidized by the addition of 30% hydrogen peroxide (2 ml). The solution was kept at 50° for 30 minutes, cooled and saturated with sulfur dioxide (generated by the action of conc. $H_2SO_4$ on $Na_2SO_3$). After several hours the crystalline acid (2) was filtered, washed with water and recrystallized from boiling water as long, pale yellow needles melting at 137°–139°, yield 2.3 g (26%) 2-Nitrophenyl acetic acid (2) high resolution MS: m/e 181.038 ($M+C_8H_7O_4N$ requires 181.038).

A mixture of piperonal (4) (1 g., 0.0066 mole), nitromethane (1.5 ml), ammonium acetate (0.072 g.) and acetic acid (5.5 ml.) was refluxed with stirring for two hours. Th reaction mixture was cooled, and bright yellow needles were filtered off, washed with cold ethanol and dried, m.p. 155°–157°, yield 1.05 g. (80%) 3,4-methylenedioxy-$\beta$-nitrostyrene (5).

High resolution MS: m/e 193.023 ($M+C_9H_7O_4N$ requires 193.038).

A rocking autoclave was charged with 7 g. (0.036 mole) of (5), 2.3 g. of 10% palladium-carbon, 7.3 ml of conc. hydrochloric acid, and the total volume was adjusted to 125 ml by addition of distilled water. The mixture was hydrogenated at 55° and an initial pressure of 800 p.s.i. for 4 hours. The reaction mixture was filtered through celite to remove the catalyst and then evaporated to dryness under reduced pressure. Benzene was added to the residue to remove traces of water. The hydrochloride (6), which appeared as a colorless, solid residue, was triturated with 3×10 ml portions of acetone and dried at 70° in a vacuum oven. The dried crystals identified as $\beta$-(3,4-Methylenedioxy) phenylethylamine hydrochloride (6) weighed 2.66 g. (71%), m.p. 207°–209°.

High resolution MS: m/e 165.083 ($M+C_9H_{11}O_2N$ requires 165.079)

A solution of 11.92 g (0.065 mole) of 2-nitrophenyl acetic acid (2) and 40 ml of thionyl chloride in 70 ml of chloroform was heated at 40° for 30 minutes. After evaporation under reduced pressure, the reaction solution gave the acid chloride (3), (13.1 g.) as a brown liquid. $\beta$-(3,4-Methylenedioxy) phenylethylamine hydrochloride (6), (13.2 g., 0.065 mole) was dissolved in 60 ml of water, and 40 ml of 2% NaOH solution was added to it. This basic solution was extracted with 3×40 ml of $CHCl_3$. The combined $CHCl_3$ extracts after evaporation gave 10.2 g. of free amine as a yellow oil which was taken up in 200 ml of 2% NaOH solution. To this cooled and vigorously stirred solution of the amine, the acid chloride (3) was added dropwise. The reaction mixture stirred overnight and the white residue obtained after filtration was washed with water and dried. Crystallization with MeOH gave 15 g (70%) of $\beta$-(3,4-Methylenedioxy)-phenylethyl-o-nitrophenylacetamide (7) in the form of white needles m.p. 116°–118°, IR (KBr) 3300 and 1645 cm$^{-1}$; $^1$H NMR (CDCl$_3$) $\delta$ 8.12 (1H, dd, J=8,3 Hz, H-Ar-o-NO$_2$), $\delta$ 7.53 (3H,m m 3H-Ar-NO$_2$), $\delta$ 6.61 (3H, m, 3H-Ar), $\delta$ 5.95 (2H, s —OCH$_2$O—), $\delta$ 3.85 (2H, s, Ar-CH$_2$CO-), $\delta$ 3.5 (2H, dd, J=13, 7 Hz, —CH$_2$NHCO—), $\delta$ 2.75 (2H, dd, J=13,7 Hz, —CH$_2$Ph—). Anal. Calcd. for $C_{17}H_{16}O_5N_2$: C, 62.19; H, 4.88: N, 8.54. Found: C, 61.98; H, 4.99; N, 8.41.

Phosphorus oxychloride (2 ml) was added dropwise to a stirred and refluxing solution of 100 mg (0.003 mole) of (7) in 5 ml of dry acetonitrile; and the reaction mixture was further refluxed for 2 hours. Excess POCl$_3$ was evaporated under reduced pressure, and the residual gum was dissolved in a minimum amount of acetonitrile (3–5 ml) diluted with 10 ml of ethylacetate. The resulting turbid mixture was washed with 2×15 ml of saturated NaHCO$_3$. Upon standing the clear organic layer gave 0.08 g. (84%) of 1-(2'-Nitrobenzyl)-6,7-methylenedioxy-3,4-dihydroisoquinoline (8) in the form of yellowish brown needles m.p. 163°–165°; $^1$H NMR (CDCl$_3$) $\delta$ 8.10 (1H, dd, J=8,3 Hz, H-3'), $\delta$ 7.40 (3H, m, H-4', H-5'. H-6'), $\delta$ 7.06 (1H, s, H-5), $\delta$ 6.71 (1H, s, H-8), $\delta$ 6.00 (2H, s, —OCH$_2$O—), $\delta$ 4.40(2H, br s, —CH$_2$-Ph—), $\delta$ 3.60(2H, dd, J=13,7 Hz, H-3), $\delta$ 2.60 (2H, dd, J=13,7 Hz, H-4). Anal. Calcd. for $C_{17}H_{14}O_4N_2$: C, 65.80; H, 4.52; N, 9.03. Found: C, 65.58; H, 4.86; N, 9.15.

A mixture of 100 mg of (8) (0.003 mole) and 250 mg of K$_2$Cr$_2$O$_7$ in 3 ml of 70% acetic acid was refluxed for 4 hours. The reaction mixture was cooled and diluted with 2 ml of water, neutralized with 10 ml of saturated NaHCO$_3$ solution, and extracted with 3×20 ml of chloroform. The chloroform extract was evaporated to give crude, 61 mg (59%). This was purified by chromatography on basic alumina (grade 3, 7 g) column using benzene:CHCl$_3$ (1:1) as eluent. The bright yellow eluate on evaporation gave 46 mg of yellowish needles of 1-(2'-Nitrobenzoyl)-6,7-methylenedioxy isoquinoline (9) m.p. 249°–251° (dec.); $^1$H NMR (CDCl$_3$) $\delta$ 7.35–8.50(6H, m, 6 Ar-H); 7.19 (1H, s, H-8), 7.17 (1H, s, H-5) 6.20(2H, s, —OCH$_2$O—). Anal Calcd. for $C_{17}H_{10}O_5N_2$: C, 63.40; H, 3.10; N, 8.69. Found: C, 62.56; H, 3.06; N, 8.16.

1-(2'-Nitrobenzoyl)-6,7-methylenedioxy isoquinoline (9), 0.5 g., 0.0015 mole) was taken up in 30 ml of ethanol, and 1.2 g. of Raney Nickel was added. The reaction mixture was hydrogenated for 24 hours at 30 p.s.i. in a Parr Pressure Reaction Apparatus. After filtration through Celite and concentration to dryness, a 50 mg portion of the resulting white solid was taken up in 1.7 ml of CH$_3$OH and 1.7 ml of 2N H$_2$SO$_4$. After cooling to 0°, 0.17 ml of 1N NaNO$_2$ was added. The reaction mixture was heated on a steam bath for 30 minutes, cooled, basified with aqueous NH$_3$, and extracted with 3×5 ml of CH$_2$Cl$_2$. Evaporation of the organic layer gave a yellow crystalline residue (44 mg). A single crystallization from CHCl$_3$ gave 23 mg (51%) of liriodenine (11), m.p. 283°–286°. Upon taking a mixed mp with authentic sample of liriodenine, no depression in the mp was observed. The I.R. spectrum of (11) was superimposable with I.R. spectrum of the authentic sample. The NMR spectrum of both authentic liriodenine and (11) showed similar peaks, and finally the identity was confirmed by tlc and co-tlc (sil G, 4% MeOH).

SYNTHESIS OF LIRIODENINE

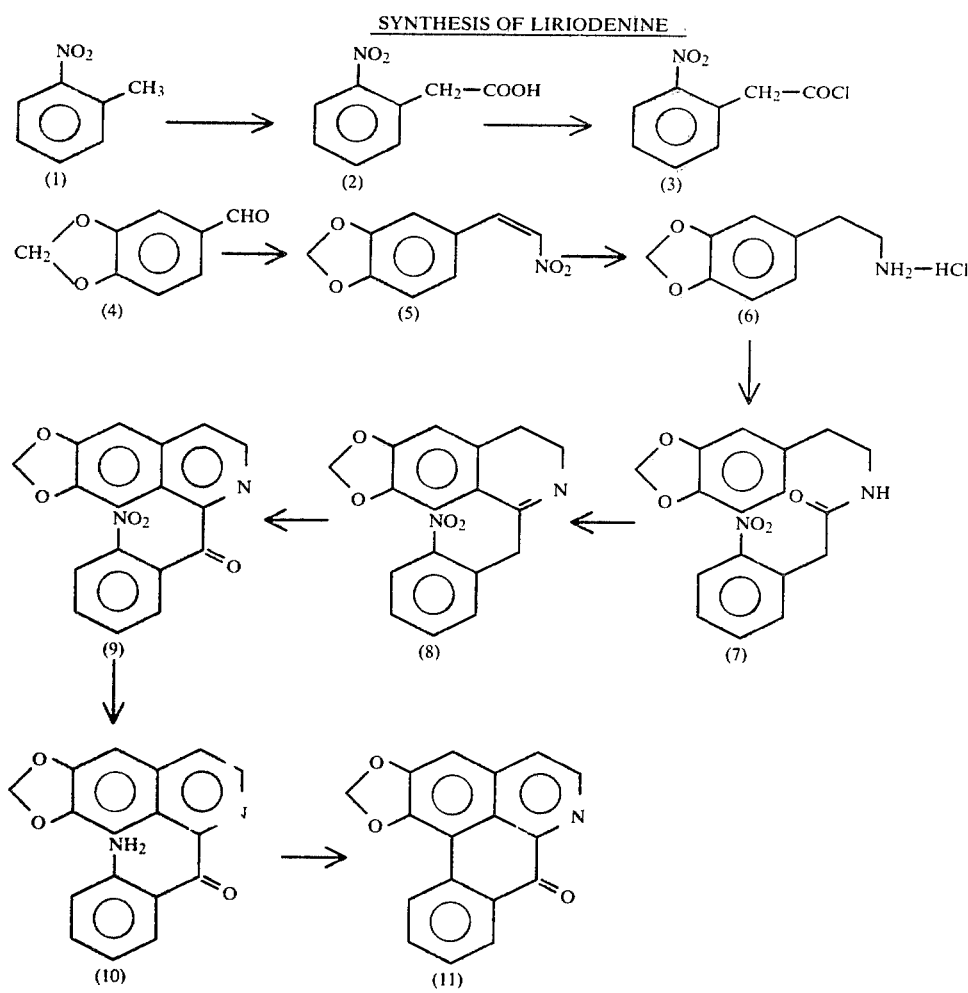

EXAMPLE V

Liriodenine methiodide was prepared from the liriodenine isolated or prepared in accordance with Examples III or IV. A 2.71 g. sample of liriodenine was refluxed in 30 ml of chloroform and then 10 ml of iodomethane was added. After 24 hours at reflux, the solution was cooled, excess iodomethane removed, and the red crystals filtered. Crystallization from methanol yielded 2.24 g. liriodenine methiodide, mp 235 d.

EXAMPLE VI

Oxoglaucine was prepared by oxidation of glaucine. 2.4 g. of glaucine in 75 ml. of acetone was oxidized by adding a solution of 6 g. of potassium permanganate in 450 ml. of acetone dropwise over 2 hours followed by stirring for 6 hours. Then another 6 g. of potassium permanganate in 450 ml. of acetone was added and allowed to stir for 12 hours. The suspension was filtered through celite and the clear orange solution was evaporated to dryness. Crystallization from a small volume of chloroform yielded 0.578 g. of orange needles of oxoglaucine having a mp 224°–225° C. Recrystallization yielded orange needles, mp 229°–230° C., of oxoglaucine which identity was confirmed by comparison of the mp, mmp, TLC, and IR, obtained using the same procedure as in Example II, with those of a known sample of oxoglaucine.

EXAMPLE VII

Oxoglaucine methiodide was prepared from oxoglaucine in accordance with the process of Example V. A 31 mg sample of oxoglaucine was refluxed in 8 ml of acetone until it completely dissolved (approximately 30 minutes) and then 0.75 ml of iodomethane was added. The solution was refluxed until it became brown. The crystals were then collected by filtration to yield 15 mg of the methiodide salt, mp 255 d.

EXAMPLE VIII

Qualitative evaluation of antimicrobial activity of the inventive extracts, fractions, and pure compounds was accomplished using an agar well diffusion assay. As set out hereinabove, the inventive compositions were tested for activity against the following microorganisms: *Staphylococcus aureus* ATCC 6538; *Escherichia coli* ATCC 10536; *Mycobacterium smegmatis* ATCC 607; *Pseudomonas aeruginosa* ATCC 15442; *Candida albicans* ATCC 10231; *Saccharomyces cerevisiae* ATCC 9763; and *Aspergillus niger* ATCC 16888. In addition, the compounds of the preferred embodiments were also tested against *Bacillus subtilis* ATCC 6633. Bacterial test organisms were cultured in Eugonagar and Eugonbroth (BBL), and fungi and yeasts were cultured in Mycophil (BBL) agar and broth.

Plates for assay were prepared by uniformly seeding sterile, partially cooled, molten agar with dilutions of test organisms grown in broth or suspensions of conidia produced on agar slants (*A. niger*). The seeded agar medium was dispensed into 100×15 mm sterile petri dishes (15 ml per dish). Cylindrical plugs were removed from the solidified agar plates, using a sterile cork borer, to produce wells having a diameter of approximately 11 mm. One hundred microliters of a solution or suspension of an extract, fraction, or pure compound was added to each well. The extracts and fractions were tested as solutions or suspensions in a concentration of 20 mg/ml; pure compounds were tested at 1 mg/ml. When solvents other than water were required to dissolve extracts or compounds, solvent blanks were run against each test organism.

Plates prepared as described above were incubated as follows: Bacteria were grown at 37° C. for 24 hours, with the exception of *M. smegmatis*, which grows more slowly and requires incubation at 37° C. for 48 hours, before reading. Fungi or yeast were incubated at 25° C. for 24 hours, before growth was evident.

Antimicrobial activity was recorded as the width (in mm) of the clear zone of inhibition surrounding the agar well. Results for those samples which exhibited antimicrobial activity are shown in Table 2.

except *M. smegmatis*, which was read at 72 hours. The concentration µg/ml of the tube of highest dilution which was free from growth was recorded as the minimal inhibitory concentration in Table 3.

TABLE 3

| Compound | Minimum Inhibitory Concentration (µg/ml) of Active Compounds | | | | |
|---|---|---|---|---|---|
| | S. aureus | B. Subtilis | M. Smegmatis | C. Albicans | S. cerevisiae |
| 1. liriodenine | 3.1 | 0.39 | 1.56 | 6.2 | 6.2 |
| 2. liriodenine methiodide | 6.2 | 3.1 | 3.1 | 0.78 | 3.1 |
| 3. Oxoglaucine methiodide | 25 | 25 | 25 | 1.56 | 25 |
| 4. dehydroglaucine | 25 | 25 | 25 | 25 | 50 |
| 5. streptomycin* sulfate | 3.1 | 1.56 | 0.78 | — | — |
| 6. amphotericin B* | — | — | — | 0.78 | 0.78 |

*Common antibiotics used as controls.

As may be appreciated from the data in Table 3, liriodenine and liriodenine methiodide show in vitro activity comparable to that of streptomycin sulfate and amphotericin B. Dehydroglaucine has a similar spectrum of activity to liriodenine and liriodenine methiodide but is not as potent. Oxoglaucine methiodide has a similar activity to dehydroglaucine but is particularly active against *C. albicans*.

EXAMPLE X

Evaluation of antimicrobial activity of the compositions of the invention against plant pathogenic microorganisms was accomplished by spraying the compounds on the test plant in a composition comprising about 300 ppm of the active ingredient. As mentioned hereinbefore, liriodenine, liriodenine methiodide and oxoglaucine methiodide were tested for activity against the following microorganisms: *Puccinia graminis* f. sp. *tritici* race 15B-2; *Plasmoporo viticola; Erysiphe polygoni; Phytophthora infestans; Botrytis fabae; Piricularia oryzae;* and *Helminthosporium teres*. The test organisms cultured and tested as described hereinbelow. The inventive

TABLE 2

| | Antimicrobial Activity of Extracts, Fractions and Compounds | | | | | |
|---|---|---|---|---|---|---|
| Sample | S. aureus | B. subtilis | M. smegmatis | C. albicans | S. cerevisiae | A. niger |
| alcohol extract | 4 mm | not tested | 10 mm | 2 mm | not tested | 5 mm |
| Tertiary nonphenolic fraction | 8 mm | not tested | 12 mm | 5 mm | not tested | 9 mm |
| fraction 12-19 | 3 mm | not tested | 2 mm | 1 mm | not tested | — |
| fraction 33-40 | 5 mm | not tested | 10 mm | 3 mm | not tested | 10 mm |
| liriodenine | 5 mm | 8 mm | 11 mm | 3 mm | 5 mm | 11 mm |
| liriodenine methiodide | 6 mm | 6 mm | 14 mm | 17 mm | 15 mm | 4 mm |
| dehydroglaucine | 4 mm | 7 mm | 8 mm | 6 mm | 6 mm | — |
| oxoglaucine methiodide | 9 mm | 9 mm | 10 mm | 10 mm | 11 mm | — |

EXAMPLE IX

Quantitative assay of antimicrobial activity of the inventive compositions against selected test organisms was made using a two-fold serial dilution in Eugonbroth or Mycophil broth. The concentration of pure alkaloids in the initial dilution tube was 50 µg/ml. Streptomycin sulfate (Nutrional Biochemical) and amphotericin B (Calbiochem "A" grade) at the same concentrations as above were used as standard antibiotics for comparison with the activities of the alkaloids against bacteria and yeast species, respectively. Cultures used in the serial dilution assay included *S. aureus, B. subtilis, M. smegmatis, C. albicans,* and *S. cerevisiae*. Readings were taken after incubation times of 24 hours for all organisms compositions are applied via each plant disease group's overhead mechanical sprayer at a speed setting of 2.3 and 60 psi air pressure. Plant foliage is treated by overhead vertical fan nozzle (T-jet No. 6501; No. 225 core) and two 45° horizontal (¼ NN, No. 2 tip, No. 215 core). The compounds were tested as solutions or suspensions of the compound. Antimicrobial activity and phytotoxicity ratings were determined by visual observation. None of the tested compositions exhibited any phytotoxicity. Results for the compounds tested are shown in Table 4 in which antimicrobial activity is indicated as follows: A (97-100% disease control); B (90-96% disease control); C (disease control, but less than 50%).

The bioassay of the pathogenic organisms and screening techniques utilized for the organisms is as follows:

A. *Piricularia oryzae* (Rice Blast)

Rice plants (var. Nova 66) were trimmed to a height of approximately 5 inches, 24 hours prior to chemical application. This procedure provided plants of uniform height and permitted rapid inoculation of treated plants.

*Piricularia oryzae* was cultured on wheat dextrose agar (WDA) plates for 14 days at ambient temperature and normal room light intensity. Spores were harvested by adding deionized water containing 2 g. gelatin and 0.5 g. sodium oleate per liter to the WDA plates and scraping the agar surface with a rubber policeman or other similar blunt object. The spore suspension was filtered through cheesecloth to remove mycelial and agar fragments and then adjusted to a concentration of $7.5-10\times10^4$ spores/ml.

The Rice plants were inoculated by spraying the leaves and stems with an air brush until a uniform film of inoculum was observed on the leaves. The inoculated plants were incubated in a humid environment (75°-85° F.) for 24 hours prior to being placed in a greenhouse environment.

Treatment comparisons were made 7-8 days after inoculation. Initial rice blast lesions appeared as small brown necrotic spots on the foliage. The typical lesion was eliptical, 1-2 cm long with a large necrotic gray center and brown margins.

B. *Erysiphe polygoni*—(Bean Powdery Mildew)

Bean plants (var. Dwarf Hort) were thinned to two plants per pot for 24 hours prior to chemical application.

*Erysiphe polygoni* was cultured on beam leaves for 10-21 days under existing greenhouse conditions. Spores were harvested by adding deionized water containing 0.5 ml of Tween 80 per 500 ml water to a quart jar containing excised mildew infested bean leaves. The spores were loosened from the leaf surface by shaking the jar. The resulting suspension was filtered through cheesecloth to remove plant debris and adjusted to $2-2.5\times10^4$ spores per ml.

Bean plants were inoculated by spraying the leaves and stems with inoculum until a uniform film of inoculum is observed on the plant. The inoculated plants were maintained under existing greenhouse conditions.

Treatment comparisons are made 8-10 days after inoculation. Typical bean powdery mildew signs are circular white mycelial mats (fructifications) on the leaf surface.

C. *Botrytis fabae*—(Broad Bean Gray Mold Leaf Spot)

Broad bean plants (*Vicia faba*) were trimmed to a height of approximately 4½ inches, 24 hours prior to chemical application. This procedure provided plants of a uniform height and permitted rapid and uniform inoculation of treated plants.

*Botrytis fabae* was cultured on oatmeal agar (OA) slants for 21 days at ambient temperature and low light intensity. Spores were harvested by adding deionized water to the OA slants and scraping the agar surface with a rubber policeman or similar blunt object. The spore suspension was filtered through cheesecloth to remove mycelial and agar fragments and then adjusted to a concentration of 175-200,000 spores per ml with an inoculation medium. The inoculation medium (20 g. glucose, 1 g. ammonium phosphate, 2 g. potassium nitrate, 10 mg. ascorbic acid, 1500 ml deionized water and 500 ml apple juice) provided improved spore germination on the surface of the broad bean leaves and stems.

The broad bean plants were inoculated by spraying the foliage with the fungicide group's overhead mechanical sprayer. Inoculated plants were then incubated in a humid environment at 75°-85° F. for 66 hours.

Treatment comparisons were made 66-68 hours after inoculation. Typical broad bean chocolate leaf spot symptoms appeared as regular circular to lanceolate lesions on plant leaves and stems.

D. *Plasmopora viticola*—(Grape Downy Mildew)

Grape seedlings, derived from Foch grape seeds, 4-5 inches tall were used.

*Plasmopora viticola* was cultured on grape leaves by placing inoculated seedlings in a humidity cabinet for 48 hours at 65°-70° F., then into a growth room at 65°-70° F. and moderate light intensity for 4 days. On the 6th day after inoculation, the inoculated grape seedlings were placed back into the original humidity cabinet. Treatment comparison was made 7 days after inoculation by observing the fungal growth on the leaf undersurface.

The grape plants were inoculated by spraying the leaves with a hand held air brush until small uniform droplets of inoculum are observed on the leaves. The inoculated plants were incubated in a humid environment at 65°-70° F. for 48 hours prior to being placed in a growth room.

Treatment comparisons were made 7 days after inoculation. Typical grape downy mildew symptoms appear on the upper leaf surface as pale-yellow spots variable in size and form, frequently circular without a distinct line of demarcation. Under humid conditions the lower leaf surface is covered by consipicuous fungal growth.

E. *Puccinia graminis* f. sp. tritici race 15B-2 (Wheat Stem Rust)

Seven-day-old wheat plants (var. Wanser) were trimmed to approximately 2½ inches, 24 hours prior to chemical application to provide a uniform plant height and to facilitate uniform inoculation.

The wheat stem rust was cultured on wheat seedlings (var. Wanser) for a period of 14 days under existing greenhouse conditions.

A spore suspension of *Puccinia graminis* f. sp tritici race 15B-2 was made by excising infected wheat leaves and placing the leaves into a pint jar containing water and the surfactant "Tween 80" (1 drop/100 cc). The surfactant serves to free the rust grediospores from the sori and improves inoculum retention when applied to plant foliage. The resulting spore suspension was filtered through cheesecloth to remove the leaves and assorted other plant debris. The spore concentration was not adjusted, but a minimum of $2.5\times10^4$ spores per mil are required to obtain an acceptable disease level.

Wheat plants were inoculated by applying the stem rust spore suspension until run-off with a DeVilbiss atomizer at 5 psi air pressure. After inoculation, the plants were placed into a humid environment at approximately 68° F. A timer was used to permit 12 hours of continuous darkness followed by a minimum of 3-4 hours of light with an intensity of 500 ft. candles. The temperature in the chamber did not exceed 85° F. At the end of the light period, the fogger was turned off and vented to allow the plants to dry slowly prior to being placed into a greenhouse environment.

The plants were permitted to grow under greenhouse conditions for a period of 2 weeks prior to making treatment comparisons. Wheat stem rust is characterized by brick red spores in irregularly shaped sori on the leaves and stems of wheat seedlings.

ment at 75°-80° F. for 24 hours prior to being placed in the greenhouse at 70°-75° F.

Treatment comparisons were made 6-7 days after inoculation. Typical barley net blotch symptoms initially appear as irregular sunken water-soaked areas which become necrotic as the lesions enlarge.

TABLE 4

Antimicrobial Activity of Compounds Specifically Against Plant Pathogenic Microorganisms

| Sample | Puccinia graminis | Plasmopora viticola | Erysiphe polygoni | Phytophthora infestans | Botrytis fabae | Piricularia oryzae | Helminthosporium teres |
|---|---|---|---|---|---|---|---|
| liridenine | B | A | B | A | A | A | A |
| liriodenine methiodide | C | B | C | C | C | C | C |
| oxyoglaucine methiodide | C | B | C | C | C | C | C |

F. *Phytophthora infestans*—(Tomato Late Blight)

Tomato (var. Rutgers) seedlings, 2½-3 inches tall, were fertilized with a water soluble fertilizer 4-5 days prior to chemical application to promote rapid succulent growth and better symptom expression.

The pathogen was grown on lima bean agar for 12-15 days at 60° F. and the fungal growth removed by the agitation of a rubber policeman or a glass rod over the surface of the agar in the presence of deionized water. The inoculum was strained through cheesecloth to remove mycelial and agar fragments and the spore concentration adjusted to 50-60,000 spores/ml.

The spore suspension was applied with a DeVilbliss atomizer at 8-10 psi air pressure onto the leaf undersurface until fine droplets are formed.

Inoculated seedlings were then placed in a humid environment at 60°-62° F. for 40-45 hours, prior to being placed in the greenhouse at 70°-75° F.

Treatment comparisons were made 5-6 days after inoculation. Initially, typical tomato late blight symptoms appear as irregular, greenish-black, water-soaked patches which enlarge and become brown, with a firm corrugates surface. Severe infection will resemble frost damage.

G. *Helminthosporium teres*—(Barley Net Blotch)

Barley plants (var. Besbar) were trimmed to a height approximately 2½ inches, 24 hours prior to chemical application. This procedure provides plants of a uniform height and permits rapid inoculation of treated plants.

*Helminthosporium teres* was cultured on potato-dextrose agar (PDA) slants for 14 days at ambient temperature and low light intensity. Spores were harvested by adding deionized water to PDA slants and scraping the agar surface with a rubber policeman or similar blunt object. The spore suspension was filtered through cheesecloth to remove mycelial and agar fragments and then adjusted to a concentration of 15-20,000 spores/ml. One drop (0.05 ml) of Tween 80 was added to 100 cc inoculum to provide a more even spore distribution on the surface of the barley leaves.

The barley plants were inoculated by spraying the foliage of the plants with a hand sprayer until small droplets of the inoculum are observed on the leaves. Inoculated plants were incubated in a humid environ- The present invention has been described in detail with particular reference to the preferred embodiments thereof; howeer, it is understood that modifications may be made without departing from the spirit and scope of the invention.

I claim:

1. An antimicrobial composition comprising a compound or mixture of compounds selected from the group consisting of liriodenine, liriodenine methiodide, dehydroglaucine, oxoglaucine methiodide and mixtures thereof in admixture with a non-toxic pharmaceutically acceptable or non-phytoxic agriculturally inert carrier in a therapeutically effective concentration.

2. The antimicrobial composition of claim 1 wherein said antimicrobial agent is liriodenine.

3. The antimicrobial composition of claim 1 wherein said antimicrobial agent is liriodenine methiodide.

4. The antimicrobial composition of claim 1 wherein said antimicrobial agent is dehydroglaucine.

5. The antimicrobial composition of claim 1 wherein said antimicrobial agent is oxoglaucine methiodide.

6. The process of detoxifying fungal organisms infecting plants which consists essentially of administering to said plant a composition consisting of a compound selected from the group consisting of liriodenine, dehydroglaucine, liriodenine methiodide and oxoglaucine methiodide in admixture with a non-phytotoxic agriculturally inert carrier, said compound being in a disease control effective concentration.

7. An antimicrobial composition effective for the treatment of wheat stem rust, grape downy mildew, bean powder mildew, tomato late blight, broad beam gray mold leaf spot, rice blast and bareley net blotch comprising a compound or mixture of compounds selected from the group consisting of liriodenine, liriodenine methiodide and oxoglaucine methiodide and mixtures thereof in admixture with a non-phytoxic, agriculturally inert carrier in a disease control effective concentration.

8. The antimicrobial composition of claim 7 wherein said antimicrobial agent is liriodenine.

9. The antimicrobial composition of claim 7 wherein said antimicrobial agent is liriodenine methiodide.

10. The antimicrobial composition of claim 7 wherein said antimicrobial agent is oxoglaucine methiodide.

* * * * *